United States Patent [19]

Nishihira et al.

[11] Patent Number: 5,834,615

[45] Date of Patent: Nov. 10, 1998

[54] PROCESS FOR PRODUCING DIARYL CARBONATE

[75] Inventors: Keigo Nishihira; Shuji Tanaka; Katsumasa Harada; Ryoji Sugise, all of Ube, Japan

[73] Assignee: Ube Industries, Ltd., Ube, Japan

[21] Appl. No.: 936,513

[22] Filed: Sep. 24, 1997

[30] Foreign Application Priority Data

Sep. 27, 1996 [JP] Japan .................................. 8-256960

[51] Int. Cl.⁶ .................................................. C07C 68/00
[52] U.S. Cl. .......................... 558/274; 558/271; 558/272; 558/273
[58] Field of Search ................... 558/271, 272, 558/273, 274

[56] References Cited

U.S. PATENT DOCUMENTS

| | | |
|---|---|---|
| 4,012,406 | 3/1977 | Buysch et al. . |
| 4,544,507 | 10/1985 | Foley . |
| 4,874,888 | 10/1989 | Shiomi et al. . |
| 5,210,268 | 5/1993 | Fukuoka et al. . |
| 5,648,510 | 7/1997 | Harada et al. . |

FOREIGN PATENT DOCUMENTS

| | | |
|---|---|---|
| 0 737 665 | 10/1996 | European Pat. Off. . |
| 0 795 539 | 9/1997 | European Pat. Off. . |
| 49-42621 | 4/1974 | Japan . |
| 52-43826 | 11/1977 | Japan . |
| 54-41813 | 4/1979 | Japan . |
| 54-84513 | 7/1979 | Japan . |
| 54-84514 | 7/1979 | Japan . |
| 54-100312 | 8/1979 | Japan . |
| 56-2541 | 1/1981 | Japan . |
| 56-8019 | 2/1981 | Japan . |
| 57-42655 | 3/1982 | Japan . |
| 57-42656 | 3/1982 | Japan . |
| 57-47658 | 10/1982 | Japan . |
| 58-50977 | 11/1983 | Japan . |
| 59-80630 | 5/1984 | Japan . |
| 3-291257 | 12/1991 | Japan . |
| 4-9358 | 1/1992 | Japan . |
| 4-211038 | 8/1992 | Japan . |
| 4-224547 | 8/1992 | Japan . |
| 4-235951 | 8/1992 | Japan . |

*Primary Examiner*—Michael G. Ambrose
*Attorney, Agent, or Firm*—Finnegan, Henderson, Farabow, Garrett & Dunner, L.L.P.

[57] ABSTRACT

A high purity diaryl carbonate is produced with a high efficiency by reacting carbon monoxide with an alkyl nitrite and/or an alkyl alcohol; reacting the resultant dialkyl oxalate with a hydroxyaryl compound, for example, phenol; decarbonylating the resultant diaryl oxalate to produce a diaryl carbonate and carbon monoxide; and collecting the diaryl carbonate from the decarbonylation reaction product mixture, the carbon monoxide produced in the decabonylation step being optionally reused for the production of the dialkyl oxalate.

9 Claims, 2 Drawing Sheets

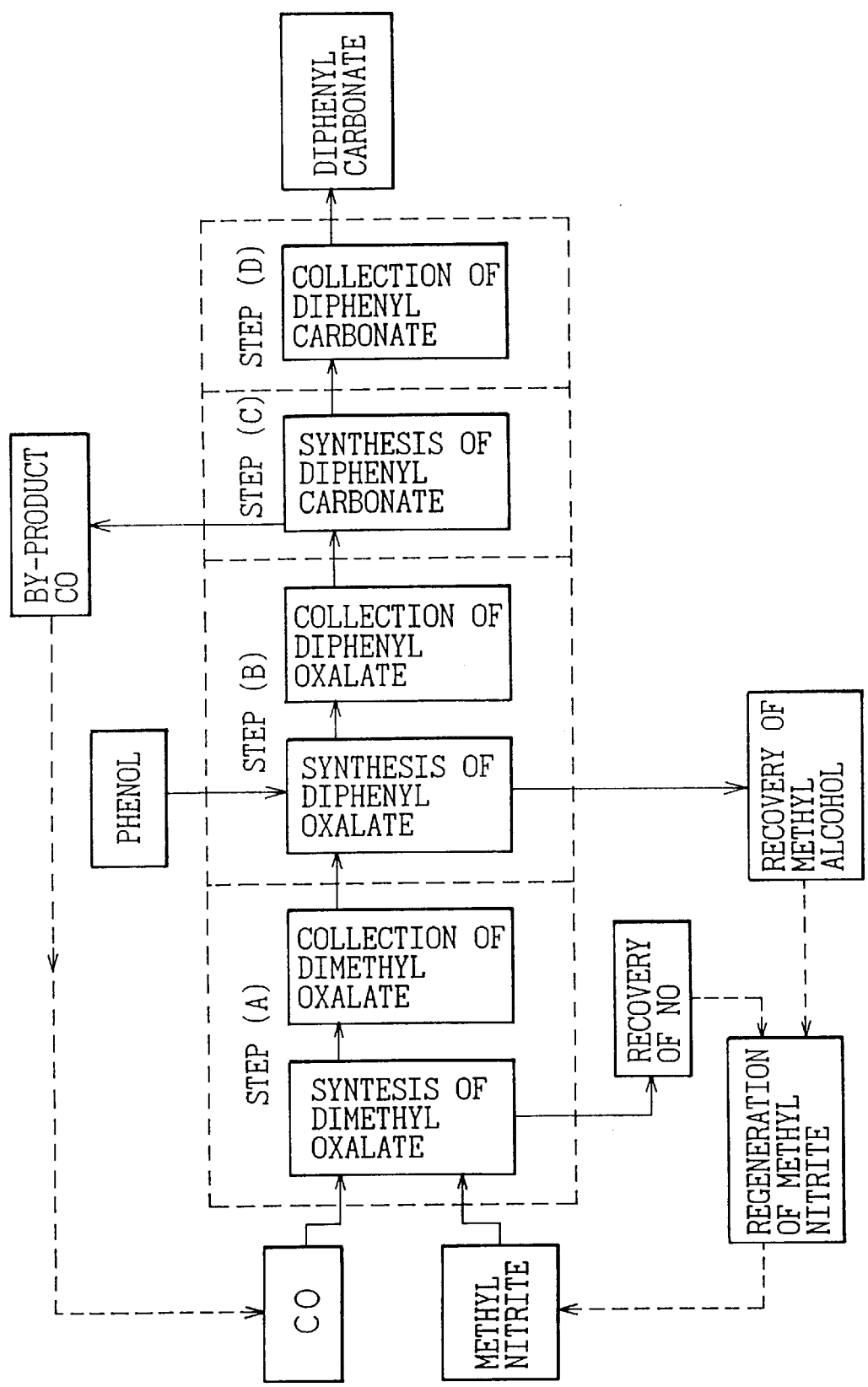

PROCESS FOR PRODUCING DIARYL CARBONATE

BACKGROUND OF THE INVENTION

1. Field of the Invention

The present invention relates to a process for producing a diaryl carbonate. More particularly, the present invention relates to a process for producing a diaryl carbonate from carbon monoxide, an alkyl nitrite and/or an alkyl alcohol and an hydroxyaryl compound, by a non-phosgene method.

The diaryl carbonate is useful as a material for producing polycarbonate resins which are useful for producing various electrical and electronic articles and chemical products, by condensation-polymerizing with polyhydroxyl compounds, for example, bisphenol A compounds.

2. Description of the Related Art

It is known that a diaryl carbonate, for example, diphenyl carbonate (DPC) can be produced by various conventional processes. For example, the diaryl carbonate can be produced by a phosgene method in which phosgene is reacted with a phenol compound, for example, phenol or a non-phosgene method in which a dialkyl carbonate, which can be produced by a conventional synthetic method, is transesterificated with a phenol compound. These conventional processes are not satisfactory for industries due to the following reasons.

Namely, in the phosgene method for the diaryl carbonate, phosgene is a strong poisonous substance and thus must be very carefully handled, and this reaction causes the resultant reaction product mixture to contain, in addition to the target diaryl carbonate, a certain amount of halogen-containing compounds, and the removal of the halogen-containing compounds from the reaction product mixture is significantly difficult as described in Japanese Examined Patent Publication No. 58-50,977.

Also, there are non-phosgen methods for producing the diaryl carbonate including a method as disclosed in Japanese Unexamined Patent Publication No. 3-291,257 and No. 4-211,038, in which the diaryl carbonate is produced by a transesterification reaction of a dialkyl carbonate with a phenol compound; and a method as disclosed in Japanese Unexamined Patent Publication No. 4-9,358, in which an alkylaryl carbonate is subjected to a disproportionation reaction.

The method of producing the diaryl carbonate by a transesterification reaction of the dialkyl carbonate with the phenol compound is disadvantageous in that the transesterification reaction is carried out as a two step equilibrium reaction in which an alkylaryl carbonate is produced as an intermediate compound, and thus the reaction rate of the first step reaction in which the alkylaryl carbonate is produced from the dialkyl carbonate and the phenol compound is low. Accordingly, to eliminate this disadvantage, various special catalyst or complicated production processes or apparatuses have been provided as disclosed in Japanese Unexamined Patent Publication No. 4-235,951 and No. 4-224,547.

Also, the method of producing the diaryl carbonate by a disproportionation reaction of a corresponding alkylaryl carbonate is disadvantageous in that since the alkylaryl carbonate is an intermediate product of the transesterification reaction from the dialkyl carbonate into a corresponding diaryl carbonate, and the resultant reaction product mixture contains, in addition to the alkylaryl carbonate, various compounds and non-reacted starting compounds, the target alkylaryl carbonate is significantly difficult to isolate from the reaction product mixture and to produce or obtain in an industrial scale. Therefore, the disproportionation method is quite unsatisfactory for industrial utilization.

Separately, for the production of a diaryl oxalate, various methods are known. For example, Japanese Examined Patent Publication No. 52-43,826 discloses a diaryl oxalate-production method by a direct esterification reaction of oxalic acid with a phenol compound in an organic solvent in the presence of an esterification catalyst at an elevated temperature of 100° to 130° C., and Japanese Examined Patent Publication No. 56-8.019 and Japanese Unexamined Patent Publication No. 49-42,621 disclose a diaryl oxalate ester-production method by a transesterification reaction of a dialkyl oxalate with a diaryl carbonate. Also, Japanese Examined Patent Publication No. 56-2,541 and No. 57-47,658 disclose a method of producing a diaryl oxalate by a transesterification reaction of dialkyl oxalate with an aryl ester of a lower fatty acid.

The diaryl oxalate-production method by the direct esterification reaction of oxalic acid with a phenol compound is disadvantageous in that the reaction rate is very low and thus a very long time is needed to complete the reaction, and thus this method is unsatisfactory from the point of view of the industry. Also, the diaryl oxalate-production method by a reaction of a dialkyl oxalate with a diaryl carbonate or an aryl ester of a lower fatty acid is disadvantageous in that the resultant reaction product mixture contains, in addition to the target diaryl oxalate, various by-products, and thus complicated or intricate refining steps are necessary to isolate the diaryl oxalate. Also, as mentioned above, the diaryl carbonate is not easy to produce industrially and obtain commercially. Therefore this method is not satisfactory for industry.

Further separately, with respect to a decarbonylation reaction of diphenyl oxalate, "Organic Synthetic Chemistry, Vol. 5, Report 4, 1948, "Thermodecomposition of diphenyl esters of dicarboxylic acid (Second Report)", reported that diphenyl carbonate could be obtained by a thermal decomposition of diphenyl oxalate at a high temperature. However, this method is unsatisfactory in that the yield of diphenyl carbonate is low, because phenol and carbon dioxide are produced as by-products.

Also, U.S. Pat. No. 4,544,507 for P. Foley discloses a method of producing a carbonate diester by heating an oxalate diester in a solvent in the presence of an alkali metal alcolate at a temperature of 50° to 150° C. This U.S. patent, however, states only that when diphenyl oxalate was subjected, as an oxalate diester, to the above-mentioned catalytic method, the resultant product comprised, as a principal component, the diphenyl oxalate which was the starting compound. Also, the U.S. patent is quite silent as to the production of diphenyl carbonate from the diphenyl oxalate. Further, the U.S. patent does not concretely disclose a method of producing diphenyl oxalate. Namely, the U.S. patent includes no suggestion of the production of a diaryl oxalate from a combination of a dialkyl oxalate with a phenol compound or alkylaryl oxalate by a transesterification reaction.

Separately, various methods for producing dialkyl oxalate from carbon monoxide and alkyl nitrites and/or lower alkyl alcohols are disclosed in Japanese Examined Patent Publication No. 56-12,624, No. 56-28,903, No. 57-30,094 and No. 61-6,057.

However, these publications are quite silent as to a process for producing diaryl oxalate by reacting a dialkyl oxalate with a phenol compound and a process for producing a diphenyl carbonate by decarbonylation of the diaryl oxalate.

SUMMARY OF THE INVENTION

An object of the present invention is to provide a process for producing a diaryl carbonate with a high degree of purity at a high yield.

Another object of the present invention is to provide a process for producing a diaryl carbonate with simple and easy procedures without using poisonous or harmful materials and complicated or intricate procedures.

Still another object of the present invention is to provide a process for producing a diaryl carbonate from carbon monoxide, an alkyl nitrite and/or an alkyl alcohol, and a hydroxyaryl compound, with a high efficiency.

The above-mentioned objects can be attained by the process of the present invention for producing a diaryl carbonate, which comprises the steps of:

(A) reacting carbon monoxide with at least one member selected from the group consisting of alkyl nitrites and alkyl alcohols, to produce a dialkyl oxalate;

(B) reacting the dialkyl oxalate with a hydroxyaryl compound to produce a diaryl oxalate;

(C) decarbonylating the diaryl oxalate to produce a diaryl carbonate and a by-product comprising carbon monoxide; and (D) collecting the resultant diaryl carbonate from the reaction product mixture of step (C).

In an embodiment of the process of the present invention, the reaction in step (A) of the carbon monoxide with at least one member selected from the group consisting of alkyl nitrites and alkyl alcohols is carried out in the presence of a catalyst containing a platinum group metal, to produce a dialkyl oxalate; the reaction in step (B) of the dialkyl oxalate with the hydroxyaryl compound is carried out in the presence of a catalyst to produce a diaryl oxalate while recovering a resultant by-product comprising an alkyl alcohol, and returning the recovered alkyl alcohol to step (A) for the production of the dialkyl oxalate; the decarbonylation reaction in step (C) of the diaryl oxalate is carried out to produce a diaryl carbonate and a by-product comprising carbon monoxide, and the resultant diaryl carbonate is collected from the reaction product mixture.

In the another embodiment of the process of the present invention, the resultant carbon monoxide produced as a by-product of the decarbonylation step (C) is collected, returned to step (A) and re-used to produce the dialkyl oxalate.

BRIEF DESCRIPTION OF THE DRAWINGS

FIG. 2 is a flow sheet showing the steps of an embodiment of the process for producing diphenyl carbonate in accordance with the present invention.

DESCRIPTION OF THE PREFERRED EMBODIMENTS

Figure 1:
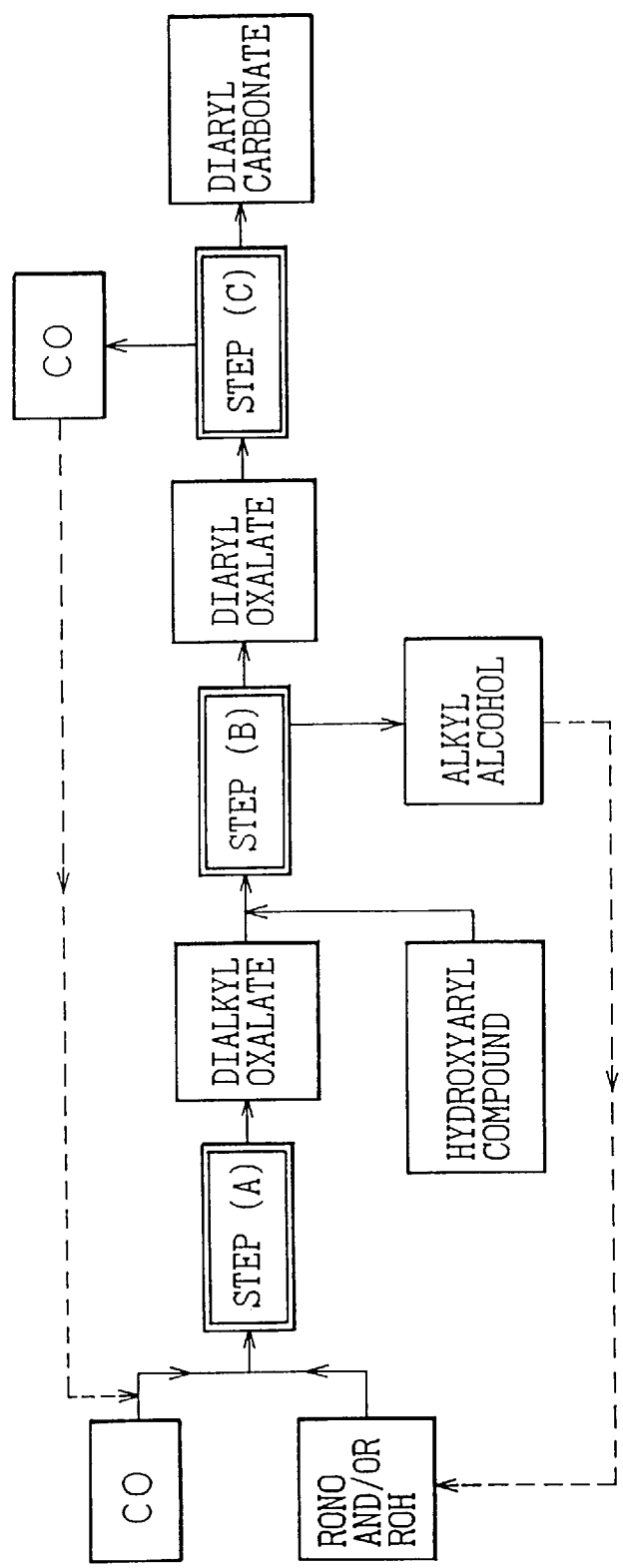
FIG. 1 is a flow sheet showing the steps of an embodiment of the process for producing a diaryl carbonate of the present invention.

The inventors of the present invention have carefully searched for a process for producing a diaryl carbonate with a high degree of purity at a high yield without using phosgene. As a result, the inventors found that a diaryl oxalate, for example, diphenyl oxalate, can be easily prepared by reacting a dialkyl oxalate, which can be prepared from carbon monoxide and an alkyl nitrite and/or an alkyl alcohol, with a hydroxyaryl compound, and the target diaryl carbonate can be easily prepared by subjecting the diaryl oxalate to a decarbonylation reaction. The present invention was completed on the basis of this finding.

In an embodiment of the process of the present invention as shown in FIG. 1, carbon monoxide and at least one member selected from alkyl nitrites and alkyl alcohols are fed into step (A) to prepare a dialkyl oxalate; the dialkyl oxalate is fed into step (B) in which the dialkyl oxalate is reacted with a hydroxyaryl compound, for example, phenol, to prepare a diaryl oxalate and a by-product comprising an alkyl alcohol; the diaryl oxalate is fed into step (C) in which the diaryl oxalate is decarbonylated to produce a diaryl carbonate and a by-product consisting of carbon monoxide; and the diaryl carbonate is collected from the reaction product mixture in step (D) (not shown in FIG. 1).

In an embodiment of the process for producing diphenyl carbonate in accordance with the present invention as shown in FIG. 2, carbon monoxide and an alkyl nitrite (methyl nitrite) are feed into step (A) wherein they are reacted in liquid or gas phase in the presence of a catalyst comprising a platinum group metal compound, to produce a dialkyl oxalate (dimethyl oxalate) and a by-product comprising nitrogen monoxide (NO), and the dialkyl oxalate (dimethyl oxalate) is collected and nitrogen monoxide is recovered. The recovered nitrogen monoxide is optionally supplied to a procedure for regenerating the alkyl nitrite for step (A).

Then, the collected dialkyl oxalate (dimethyl oxalate) and a hydroxyaryl compound (phenol) are fed into step (B) in which the dialkyl oxalate (dimethyl oxalate) is transesterified with the hydroxyaryl compound (phenol) in liquid phase in the presence of a transesterification catalyst, to prepare a diaryl oxalate (diphenyl oxalate) and a by-product comprising an alkyl alcohol (methyl alcohol), and the diaryl oxalate (diphenyl oxalate) is collected and the alkyl alcohol (methyl alcohol) is recovered. The recovered alkyl alcohol (methyl alcohol) is optionally supplied to the alkyl (methyl) nitrite-regeneration procedure.

Then, the collected diaryl oxalate (diphenyl oxalate) is fed into step (C) in which the diaryl oxalate (diphenyl oxalate) is decarbonylated in liquid phase or gas phase in the presence of a decarbonylation catalyst to produce a diaryl carbonate (diphenyl carbonate) and a by-product comprising carbon monoxide. The resultant diaryl carbonate (diphenyl carbonate) is collected in step (D). Also, the resultant carbon monoxide is recovered and optionally returned to step (A) as a material for producing the dialkyl (dimethyl) oxalate. The above-mentioned process can be continuously carried out in industrial scale to prepare a diaryl carbonate, particularly diphenyl carbonate.

In the process of the present invention, it is industrially preferable that the reaction of carbon monoxide with an alkyl nitrite in step (A) is carried out in the gas phase in the presence of a platinum group metal-containing catalyst, to produce a dialkyl oxalate and nitrogen monoxide.

Also, in step (A), it is industrially preferable that nitrogen monoxide produced as a by-product of the reaction of carbon monoxide with the alkyl nitrite is reacted with molecular oxygen and an alkyl alcohol to regenerate the alkyl nitrite, and the regenerated alkyl nitrite is returned to step (A) and re-used for the reaction of step (A), as shown in FIG. 2.

In step (A) of the process of the present invention, for example, carbon monoxide (CO) is reacted with an alkyl nitrite (RONO) and/or an alkyl alcohol (ROH) in the presence of the platinum group metal-containing catalyst in accordance with the reaction formulae (1) and (2):

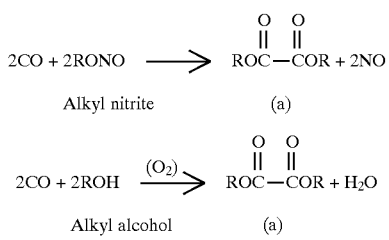

(1)
$$2CO + 2RONO \longrightarrow ROC(O)-C(O)OR + 2NO$$
Alkyl nitrite (a)

(2)
$$2CO + 2ROH \xrightarrow{(O_2)} ROC(O)-C(O)OR + H_2O$$
Alkyl alcohol (a)

In the reaction formulae (1) and (2), R represents an alkyl group.

In the reaction formula (1), the alkyl nitrite is represented by the formula RONO, and the alkyl group represented by R is preferably selected from lower alkyl groups having 1 to 6 carbon atoms, for example, methyl, ethyl, n-propyl, isopropyl, n-butyl, isobutyl, pentyl and hexyl groups. The alkyl nitrite is preferably selected from lower alkyl nitrites having 1 to 4 carbon atoms, for example, methyl nitrite, ethyl nitrite, n-propyl nitrite, isopropyl nitrite, n-butyl nitrite and isobutyl nitrite.

In the reaction formula (2), the alkyl alcohol represented by the formula ROH wherein R is as defined above. The alkyl alcohol is preferably selected from lower alkyl alcohols having 1 to 4 carbon atoms, for example, methyl, ethyl, n-propyl, isopropyl, n-butyl and isobutyl alcohols.

In step (B) of the process of the present invention, the production of a diaryl oxalate from the dialkyl oxalate and the hydroxyaryl compound is conducted in accordance with the reaction formulae (3) to (5):

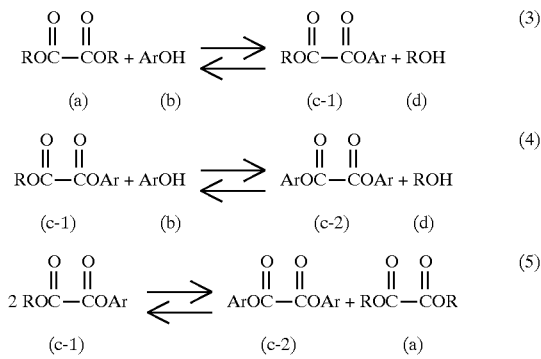

(3)
$$ROC(O)-C(O)OR + ArOH \rightleftarrows ROC(O)-C(O)OAr + ROH$$
(a) (b) (c-1) (d)

(4)
$$ROC(O)-C(O)OAr + ArOH \rightleftarrows ArOC(O)-C(O)OAr + ROH$$
(c-1) (b) (c-2) (d)

(5)
$$2\,ROC(O)-C(O)OAr \rightleftarrows ArOC(O)-C(O)OAr + ROC(O)-C(O)OR$$
(c-1) (c-2) (a)

In the reaction formulae (3) to (5), R is as defined above and Ar represents an unsubstituted or substituted aryl group.

In step (B), a dialkyl oxalate (a) and a hydroxyaryl compound are subjected to a transesterification reaction in the presence of a transesterification catalyst. The transesterification reaction is conducted in accordance with the reaction formulae (3) and (4) and an alkylaryl oxalate (c-1), a diaryl oxalate (c-2) and an alkyl alcohol (d) are produced. Also, in step (B), the alkylaryl oxalate (c-1) is disproportionated in the presence of the transesterification catalyst in accordance with the reaction formula (5), to produce a diaryl oxalate (c-2) and a dialkyl oxalate (a). The disproportionation reaction is a type of transesterification reaction. The transesterification and disproportionation reactions (3), (4) and (5) in step (B) are preferably carried out in liquid phase.

In the reaction formulae (3) to (5), the alkyl group represented by R is preferably selected from lower alkyl groups having 1 to 6 carbon atoms, as mentioned above, and the unsubstituted aryl group represented by Ar is preferably selected from phenyl and naphthyl group. Also, substituted aryl group represented by Ar preferably has at least one substituent directly bonded to an aryl ring and preferably selected from alkyl groups with 1 to 6 carbon atoms, for example, methyl, ethyl, propyl and butyl group and alkoxy groups with 1 to 6 carbon atoms, for example, methoxy, ethoxy, propoxy and butoxy groups.

In step (B), all of the reactions of the formulae (3) to (5) occur. More particularly, the transesterification reaction of the formula (3) and the disproportionation reaction of the formula (5) principally occur. Namely, the alkylaryl oxalate (c-1) and the alkyl alcohol are produced in accordance of the transesterification reaction of the formula (3) and then the alkylaryl oxalate (c-1) is principally converted by the disproportionation reaction of the formula (5), which is a type of transesterification reaction, into the diaryl oxalate (c-2) and the dialkyl oxalate (a). Accordingly, as a result of step (B), the diaryl oxalate and the alkyl alcohol is produced from the dialkyl oxalate and the hydroxyaryl compound.

In step (C), a diaryl oxalate (c-2) is subjected to a decarbonylation reaction in accordance with the reaction formula (6), optionally in the presence of a decarbonylation catalyst, to produce a diaryl carbonate (e) and carbon monoxide. This decarbonylation reaction is preferably carried out in the liquid phase.

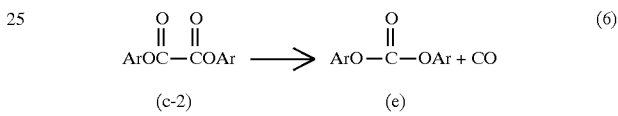

(6)
$$ArOC(O)-C(O)OAr \longrightarrow ArO-C(O)-OAr + CO$$
(c-2) (e)

In the formula (6), Ar is as defined above.

The platinum group metal-containing catalyst usable for step (A) of the process of the present invention includes platinum group metals and salts thereof, as disclosed in Japanese Examined Patent Publication No. 56-28,903, No. 56-28,904, No. 61-6,057 and No. 61-26,977.

The platinum metals include platinum, palladium, rhodium and iridium metals, and the platinum group metal salts include inorganic acid salts (for example, nitrate, sulfates, and phosphates), halides (for example, chlorides and bromides) and organic acid salts (for example, acetates and oxalates and benzoates) of the above-mentioned platinum group metals and complexes thereof.

Among the platinum group metals and salts thereof, palladium metal and salts thereof are particularly preferred. The palladium salts include inorganic acid salts (for example, nitrate, sulfate and phosphate), halides (for example, chlorides, and bromide), organic acid salts (for example, acetate, oxalate and benzoate) and complexes of palladium. The palladium complexes includes those containing, as a ligand, an alkylphosphine group (for example, trimethylphosphine group), an arylphosphine group (for example, triphenylphosphine group) an alkylarylphosphine group (for example, diethylphenylphosphine group) or an arylphosphite group (for example, triphenylphosphite group) coordinated to a palladium atom.

When the platinum group metal-containing catalyst is used, it is industrially preferable that the platinum group metal or salt thereof is carried in an amount of 0.01 to 10% by weight, more preferably 0.2 to 2% by weight, in terms of the platinum group metal, on an inactive carrier. For example, palladium metal or a salt thereof is preferably carried on an inactive carrier, for example, activated carbon, alumina (including γ-alumina and α-alumina), silica, diatomaceous earth, pumice, zeolite, molecular sieves and spinel. When a solid catalyst, in which a platinum group metal salt is carried on a carrier, is used, it is preferred that in the preparation of the catalyst, the platinum group metal salt is reduced with a reducing substance, for example, hydrogen to the corresponding platinum group metal, or before using for the reaction, the platinum group metal salt is reduced with a reducing substance, for example, carbon monoxide to the corresponding platinum group metal. The platinum group metal-containing catalyst can be produced by conventional procedures.

The platinum group metal-containing catalyst optionally contains, for example, iron or a compound thereof, as disclosed in Japanese Unexamined Patent Publication No. 59-80,630.

As the iron and iron compounds, iron metal, iron (II) compounds and iron (III) compounds can be used. The iron (II) compounds include, for example, ferrous sulfate, ferrous nitrate, ferrous chloride, ferrous ammonium sulfate, ferrous lactate, and ferrous hydroxide. The iron (III) compounds include, for example, ferric sulfate, ferric nitrate, ferric chloride, ferric ammonium sulfate, ferric lactate, ferric hydroxide, and ferric citrate. The iron and iron compounds are preferably used in an atomic ratio of platinum group metal to iron (Pt group metal/Fe) of 10000:1 to 1:4, more preferably 5000:1 to 1:3. The iron or iron compound-containing catalyst can be produced by conventional methods.

Carbon monoxide Lo be used in step (A) may be pure carbon monoxide, or may be diluted with an inert gas such as nitrogen, or may contain a small amount of hydrogen gas or methane. Also, in the process of the present invention, carbon monoxide produced as a by-product in step (C) can be advantageously used in step (A). For example, when step (A) is carried out continuously in the gas phase, carbon monoxide produced in step (C) is mixed with the regenerated gas, which will be explained hereinafter, to supplement an amount of carbon monoxide consumed in the reaction for the production of the diaryl oxalate, and the mixed gas is supplied to step (A).

When the reaction in step (A) is carried out in the gas phase, the reaction proceeds after bringing a material gas containing carbon monoxide and an alkyl nitrite into contact with the platinum group metal-containing catalyst in gas phase, as disclosed in Japanese Examined Patent Publication No. 61-6,057 and No. 61-26,977. In this case, the contact time of the material gas with the platinum group metal-containing catalyst is usually 10 seconds or less, preferably 0.2 to 5 seconds, and the reaction temperature is usually 50° to 200° C., preferably 80° to 150° C. Also, the reaction is usually carried out under a pressure of from the ambient atmospheric pressure to 10 kg/cm$^2$G, preferably from the ambient atmospheric pressure to 5 kg/cm$^2$G. As a reactor for the reaction of step (A), a single tube type or multi-tube type heat-exchange reactor is advantageously utilized.

In step (A), the content of carbon monoxide in the material gas is usually established in the range of from 2 to 90% by volume. Also, the content of alkyl nitrite in the material gas is variable in broad range. However, to obtain a satisfactory result, the content of the alkyl nitrite is preferably established in a range of 1% by volume or more, more preferably from 5 to 30% by volume.

In step (A), a dialkyl oxalate-containing reaction product is produced by the above-mentioned gas phase reaction. For example, the reaction product is introduced into a condenser to separate it into a condensed liquid fraction and a non-condensed gas fraction. In this condensation, to prevent the dialkyl oxalate being accompanied by the non-condensed gas fraction, the reaction product is preferably cooled and condensed while being brought into contact with a lower alkyl alcohol.

The condensed liquid fraction contains, in addition to the target dialkyl oxalate, small amounts of by-products, for example, a dialkyl carbonate and an alkyl formate. The by-products can be removed by a simple conventional procedure, for example, distillation, and thus a refined dialkyl oxalate can be easily collected. The collected dialkyl oxalate is supplied to step (B).

On other hand, since the non-condensed gas fraction contains, in addition to non-reacted carbon monoxide and alkyl nitrite, nitrogen monoxide produced by the above-mentioned reaction, it is industrially advantageous that the nitrogen monoxide is converted to an alkyl nitrite, and the resultant regenerated alkyl nitrite is fed into step (A), as described in Japanese Examined Patent Publication No. 61-6,057 and 61-26,977.

The regeneration of the alkyl nitrite can be effected by introducing the non-condensed gas fraction into a regeneration column, and bringing nitrogen monoxide in the non-condensed gas fraction into contact with molecular oxygen and a lower alkyl alcohol.

In this regeneration, the lower alkyl alcohol is the same as the lower alkyl alcohol to be used as a component for producing the alkyl nitrite. In the process of the present invention, preferably, the lower alkyl alcohol delivered from the reaction system of the transesterification reaction of step (B) is recovered and reused in the regeneration of the alkyl nitrite from the non-condensed gas fraction of step (A). As the molecular oxygen, oxygen gas or air is used.

Also, as a regeneration column, a conventional gas-liquid contacting apparatus, for example, a packed column, bubbling column, spray column or sieve-tray column is used.

In the above-mentioned regeneration of the alkyl nitrite, the reaction conditions are preferably controlled to an extent such that the regenerated gas delivered from the regeneration column has a content of nitrogen dioxide of 2 to 7% by volume, and thus the regenerated gas is substantially free from nitrogen monoxide and oxygen.

For this purpose, preferably the molecular oxygen is fed in an amount of 0.08 to 0.2 mole per mole of nitrogen monoxide contained in the non-condensed gas fraction introduced into the regeneration column, and the nitrogen monoxide is brought into contact with the molecular oxygen and the lower alkyl alcohol at a temperature equal to or lower than the boiling temperature of the lower alkyl alcohol under the pressure under which the regeneration reaction is carried out. The amount of the lower alkyl alcohol to be fed into the regeneration procedure is preferably 2 to 5 parts by gas volume per part by volume of the nitrogen monoxide in the non-condensed gas fraction, and the contact time is preferably 0.5 to 20 seconds. Also, when step (A) is carried out in a continuous procedure, preferably, the nitrogen component lost from the reaction system is supplemented by introducing nitrogen oxides, for example, nitrogen monoxide, nitrogen dioxide, dinitrogen trioxide and dinitrogen tetraoxide) or nitric acid into the regeneration column.

As mentioned, a gas (regeneration gas) containing the regenerated alkyl nitrite, having a restricted content of nitrogen monoxide of 2 to 7% by volume and substantially free from nitrogen dioxide and oxygen is fed into step (A). In this feeding, to supplement an amount of carbon monoxide consumed by the reaction, the carbon monoxide produced in step (C) is collected, returned to step (A) and mixed with the regeneration gas.

When the reaction of step (A) is carried out in the liquid phase, this reaction is effected by bringing, under pressure, a gas containing carbon monoxide and oxygen into contact with a mixed liquid of a lower alkyl alcohol, an alkyl nitrite and a platinum group metal-containing catalyst, as described in Japanese Examined Patent Publication No. 56-28,903 and 56-28,904. In this reaction, the reaction time is usually 5 to 60 minutes, the reaction temperature is usually 40° to 200° C., preferably, 60° to 150° C. and the reaction pressure is usually 5 to 250 kg/cm G, preferably 10 to 200 kg/cm G.

The reactor for the liquid phase reaction of step (A) is advantageously selected from cylindrical hollow column, packed column or sieve-tray column.

In the liquid phase reaction, carbon monoxide and oxygen are fed in a volume ratio of oxygen to carbon monoxide ($O_2$/CO) of 1:5 to 1:80, and alkyl nitrite is fed in a content of 8 to 50% by weight based on the total weight of the mixed liquid. The platinum group metal-containing catalyst is preferably used in the form of being carried on a carrier of, for example, activated carbon, alumina ($\gamma$-alumina or $\alpha$-alumina), or silica. The catalyst is used preferably in an amount of 0.1 ppm by weight to 2% by weight, more preferably 10 to 200 ppm by weight in terms of the platinum group metal, based on the total weight of the mixed liquid.

In the liquid phase reaction, the resultant reaction product mixture contains, in addition to the target dialkyl oxalate, by-products, for example, water, dialkyl carbonate and alkyl formate. Therefore, the reaction product mixture is introduced into a dehydration column to remove water by distillation, and then the target dialkyl oxalate is collected by a collecting procedure such as distillation.

Step (B) of the process of the present invention will be explained in detail below.

In step (B) of the process of the present invention, the dialkyl oxalate produced by step (A) is reacted with a hydroxyaryl compound, for example, phenol, to produce a diaryl oxalate as a second intermediate compound. The diaryl oxalate is collected from step (B) and fed into step (C).

In preferable reactions of step (B), for example, a dialkyl oxalate is subjected to an transesterification reaction with a hydroxyaryl compound in the presence of a transesterification catalyst, while evaporating and removing a by-product comprising an alkyl alcohol from the reaction product mixture, mainly in accordance with the reaction formula (3), to produce an alkylaryl oxalate, then the alkylaryl oxalate is subjected to a disproportionation (transesterification) reaction in the presence of the above-mentioned transesterification catalyst, while evaporating and removing a by-product comprising dialkyl oxalate, in accordance with the reaction formula (5), to produce a diaryl oxalate, and finally, the resultant diaryl oxalate is collected from the reaction product mixture.

Alternatively, a transesterification of a dialkyl oxalate with a hydroxyaryl compound in the presence of a transesterification catalyst and a transesterification of an alkylaryl oxalate with the hydroxyaryl compound in the presence of the above-mentioned transesterification catalyst in accordance with the reaction formulae (3) and (4) are carried out, and the resultant diaryl oxalate is collected.

In the above-mentioned step (B), the dialkyl oxalate, the hydroxyaryl compound and the transesterification catalyst are fed into a first reactive distillation column, to transesterify the dialkyl oxalate with the hydroxyaryl compound in the presence of the above-mentioned catalyst, a resultant first vapor fraction comprising, as a principal component, an alkyl alcohol is withdrawn from the top portion of the first reactive distillation column, and a resultant reaction product mixture in the state of a liquid is withdrawn from the bottom portion of the first reactive distillation column. The withdrawn reaction product mixture liquid is fed into a second reactive distillation column to subject the reaction product comprising an alkylaryl oxalate to a disproportionation reaction thereof and/or a transesterification reaction thereof with the hydroxyaryl compound in the presence of the transesterification catalyst, the resultant second vapor fraction comprising, as a principal component, a dialkyl oxalate and/or an alkyl alcohol from the top portion of the second reactive distillation column, and a resultant reaction product mixture in the state of a liquid and comprising, as a principal component, a diaryl oxalate is removed from the bottom portion of the second reactive distillation column.

The second vapor fraction withdrawn from the top portion of the second reactive distillation column is optionally subjected to a distillation procedure to evaporate and remove an initial distillate comprising the alkyl alcohol, and then the second distillate comprising, as principal components, the dialkyl oxalate and the hydroxyaryl compound is collected, returned to and reused in the first reactive distillation column.

Namely, in step (B), preferably a dialkyl oxalate, a hydroxyaryl compound and a transesterification catalyst are fed separately or altogether into an upper region of a plurality of trays or packing layers of the first reactive distillation column, which will be explained in detail hereinafter. Also, the reaction product mixture liquid withdrawn from the bottom portion of the first reactive distillation column is preferably fed into an upper region of a plurality of trays or packing layers to cause the desired reaction to be effected.

The first and second reactive distillation columns are preferably selected from reactive distillation columns having a plurality of distillation trays or reactive distillation columns having an upper portion thereof packed with packings, and have a theoretical step number of at least two, particularly 5 to 100, more particularly 7 to 50.

The multi-step type reactive distillation column usable for the step (B) of the process of the present invention may be selected from a tray type distillation column in which foam bell trays, perforated plate trays or sieve trays are arranged, and a packing type distillation column in which various packings, for example, Raschig rings, läsching rings or pall rings, are packed. Also, a reaction apparatus containing both the tray type and packing type distillation columns can be used for step (B).

When the reactions in step (B) is carried out in the liquid phase, while a reaction liquid flows downward in each of the first and second reactive distillation columns, preferably the reaction temperature is equal to or higher than that at which the reaction liquid comprising the starting compounds and the resultant reaction products is melted, and does not cause the reaction products, namely the alkylaryl oxalate and the diaryl oxalate to be thermally decomposed. In step (B), the reaction temperature is preferably about 50° to 350° C., more preferably 100° to 300° C., still more preferably 120° to 280° C.

The reaction pressure for step (B) may be a reduced pressure, the ambient atmospheric pressure or an increased pressure. Preferably, the reactions of step (B) is carried out at a temperature under a pressure which allow the by-products such as the alkyl alcohol and the dialkyl oxalate to evaporate. For example, when the reaction temperature is 50° to 350° C., the reaction pressure is preferably 0.01 mmHg to 100 kg/cm$^2$G, more preferably 0.1 mmHg to 50 kg/cm$^2$G. In step (B) of the process of the present invention, the reaction time, which corresponds to a residence time of the reaction liquid in the first and second reactive distillation columns when the reactive columns are multi-step type distillation columns, is variable in response to the reaction conditions and type and operational conditions of the reactive distillation columns. Usually, when the reaction temperature is about 50° to 350° C., the reaction time is about 0.01 to 50 hours, preferably 0.02 to 10 hours, more preferably 0.05 to 5 hours.

In the reaction in step (B), the molar ratio of the hydroxyaryl compound to the dialkyl oxalate to be used is variable in response to the type and amount of the catalyst and the reaction conditions. The molar ratio of the phenol compound to the dialkyl oxalate contained in the feed materials is preferably 0.01:1 to 1000:1, more preferably 0.5:1 to 20:1.

The amount of the catalyst to be used for the reaction in the step (B) is variable depending on the type of the catalyst, the type and the size of the reaction apparatus, type of each material, composition of the feed material, and reaction conditions of the transesterification reaction. The transesterification catalyst is used preferably in an amount of about 0.0001 to 50% by weight, more preferably 0.001 to 30% by weight, still more preferably 0.005 to 10% by weight, based on the total weight of the dialkyl oxalate and the phenol compound.

The catalyst (transesterification catalyst) usable for step (B) of the process of the present invention is preferably selected from conventional soluble transesterification catalysts comprising at least one member selected from complexes of alkali metals, cadmium and zirconium, lead compounds, iron compounds, copper group metal compounds, zinc compounds, organic tin compounds and Lewis acid compounds of aluminum, titanium and vanadium, for example, $Ti(OBu)_3$, $Ti(OPh)_3$, $Ti(OBu)_4$, $Ti(OPh)_4$, $Al(OBu)_3$, $Al(OPh)_3$, $VO(OPh)_3$.

The alkyl alcohol removed from the reaction system in step (B) is preferably supplied to step (A) for producing the dialkyl oxalate. For example, the first vapor fraction withdrawn from the top portion of the first reactive distillation column and comprising, as a principal component, an alkyl alcohol may be cool-condensed, and the condensed, alkyl alcohol-containing liquid fraction may be collected and supplied, as a material for regenerating the alkyl nitrite, to a regeneration column connected to the reactor of step (A). The condensed liquid fraction comprises, as a principal component, the alkyl alcohol, and thus can be fed into the regeneration column of step (A), without refining. However, if the condensed liquid fraction contains impurities, for example, phenol, it is preferable that the condensed liquid is refined by, for example, distillation, and then supplied to the regeneration procedure of the alkyl nitrite for step (A).

The reaction product mixture liquid obtained from the reactions (transesterification reaction and disproportionation reaction) of step (B) comprises as principal components, the intermediate alkylaryl oxalate (for example, methylphenyl oxalate), the target diaryl oxalate (for example, diphenyl oxalate), the by-product alkyl alcohol (for example, methyl alcohol), the by-product dialkyl oxalate (for example, dimethyl oxalate). The total amount of the by-products is very small. Therefore, the target diaryl oxalate can be easily collected from the reaction product mixture obtained from the second reactive distillation column by a conventional distillation procedure.

In a concrete example of the collection procedure, the reaction product mixture liquid obtained from step (B) is subjected to a distillation and/or an evaporation procedure by using a distillator and/or an evaporator, to separate and collect the diaryl oxalate. Otherwise, the reaction product mixture liquid is subjected to a crystallization-precipitation procedure in which the diaryl oxalate and the hydroxyaryl compound form a crystalline adduct, for example, a crystalline adduct of diphenyl oxalate with phenol in a molar ratio of 1:2, and the adduct crystals are precipitated, and the resultant precipitated adduct crystals are collected.

The reaction product mixture liquid fraction withdrawn from the bottom of the second reactive distillation column can be refined, for example, by the following procedures. The liquid fraction is fed into an evaporator, and a major portion of the liquid fraction is evaporated so as to leave the catalyst, the resultant vapor fraction is fed into a first distiller, a light fraction comprising an alkylaryl oxalate and a hydroxyaryl compound is withdrawn from the top portion of the first distiller and condensed, and a liquid fraction comprising, as a principal component, a diaryl oxalate is withdrawn from the bottom portion of the first distiller. The liquid fraction from the first distiller is fed into a second distiller and distilled therein, and a resultant vapor fraction comprising the diaryl oxalate is withdrawn from the top portion of the second distiller and collected.

The refining procedure can be carried out by using only one distiller. In this manner, the catalyst is removed from the liquid fraction delivered from step (B) by using an evaporator, the resultant vapor fraction of the evaporator is fed into the single distiller and distilled therein, the resultant light vapor fraction comprising the alkylaryl oxalate and the hydroxyaryl compound is withdrawn from the top portion of the distiller, and a liquid fraction comprising the diaryl oxalate is collected from the bottom portion of the distiller by a side cut method. In other refining procedures, the liquid fraction delivered from step (B) is distilled by the first distiller, a light vapor fraction (comprising the alkylaryl oxalate and the hydroxyaryl compound) is withdrawn and removed from the top portion of the first distiller, and a liquid fraction comprising, as a principal component, the diaryl oxalate, is withdrawn from the bottom portion of the first distiller. The withdrawn liquid fraction of the first distiller is fed into a second distiller, a resultant liquid fraction containing the catalyst is withdrawn from the bottom portion of the second distiller, and a resultant vapor fraction comprising the diaryl oxalate is withdrawn from the top portion of the second distiller and withdrawn diaryl oxalate is collected.

The collected diaryl oxalate obtained by the above-mentioned refining procedures has a high degree of purity even when the step number of the distillers is relatively small. For example, a high degree of purity of 99.0% by weight or more of diaryl oxalate can be obtained. This is because the liquid fraction obtained from step (B) contains, in addition to the target diaryl oxalate, the hydroxyaryl compound and the alkylaryl oxalate, the hydroxyaryl compound and the alkylaryloxalate have very different boiling temperatures from diaryl oxalate and thus can be easily removed from the diaryl oxalate.

When the collected diaryl oxalate is fed into step (C), a degree of purity of 99.0% by weight or more of the diaryl oxalate is satisfactory. Preferably, the contents of impurities, namely, the hydroxyaryl compound and the alkylaryl oxalate in the diaryl oxalate is respectively 1.0% by weight or less, more preferably 0.5% by weight or less, still more preferably 0.1% by weight or less.

Further, the condensed fraction collected from the top portion of the first distiller and comprising, as principal components, the alkylaryl oxalate and the hydroxyaryl component is preferably fed into the second reactive distillation column and used again therein.

The steps (C) and (D) of the process of the present invention will be further explained in detail below.

In step (C), the diaryl oxalate obtained by step (B) is subjected to a decarbonylation reaction to produce a corresponding diaryl carbonate and a by-product comprising carbon monoxide, and then in step (D) the diaryl carbonate is collected from the reaction product mixture and carbon monoxide is collected and returned to step (A) and re-used therein. The decarbonylation reaction is carried out in the presence of a decarbonylation catalyst in gas phase or liquid phase, preferably in liquid phase.

When step (C) is carried out in the liquid phase, the decarbonylation catalyst is preferably selected from those enabling the decarbonylation reaction of the diaryl oxalate to be effected at a relatively low temperature of, for example, about 100° to 350° C., and the diaryl carbonate to be obtained at a high selectivity of, for example, at least 50 molar %, particularly 60 to 100 molar %.

The decarbonylation catalyst usable for the liquid phase decarbonylation reaction preferably comprises at least one organic phosphorus compound, more preferably at least one organic phosphorus compound having at least one carbon-phosphorus bond. This type of phosphorus compound is preferably selected from organic phosphine compound of the general formula (w), organic phosphine oxide compounds of the general formula (x), organic phosphine dihalide compounds of the general formula (y) and organic phosphonium salt compounds of the general formula (z).

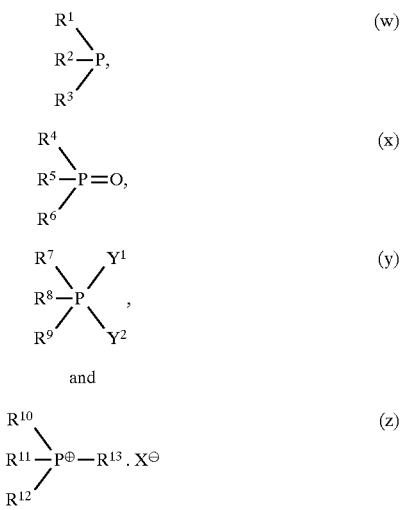

In the above general formulae (w), (x), (y) and (z), $R^1$ to $R^{13}$ represent respectively and independently from each other a member selected from the group consisting of a hydrogen atom, alkyl groups having 1 to 16 carbon atoms, aryl groups having 6 to 16 carbon atoms, substituted aryl groups, aralkyl group having 7 to 22 carbon atoms, and substituted aralkyl groups provided that at least one of $R^1$, $R^2$ and $R^3$, at least one of $R^4$, $R^5$ and $R^6$, at least one of $R^7$, $R^8$ and $R^9$ and at least one of $R^{10}$, $R^{11}$, and $R^{12}$ and $R^{13}$ are not a hydrogen atom, X represent an anionic atom or atomic group, and $Y^1$ and $Y^2$ represent respectively and independently from each other a halogen atom.

The substituted aryl groups have at least one substituent directly attached to a carbon atom located in the aryl ring structure. Also, the substituted aralkyl groups have at least one alkyl moiety and at least one substituent other than the alkyl group, and are directly attached to a carbon atom located in the aryl ring structure.

The substituent for the substituted aryl groups and the substituted aralkyl groups is preferably selected from the group consisting of halogen atoms, for example, fluorine, chlorine and bromine atoms, a nitro group, alkyl groups having 1 to 16 carbon atoms, and alkoxy groups having 1 to 16 carbon atoms.

Two of $R^1$ to $R^3$, two of $R^4$ to $R^6$, two of $R^7$ to $R^9$ and two of $R^{10}$ to $R^{13}$ may be connected or cross-linked to each other.

In the phosphorus compounds of the formulae (w) to (z), the alkyl groups represented by $R^1$ to $R^{13}$ and having 1 to 16 carbon atoms include methyl, ethyl, n-propyl, isopropyl, n-butyl, isobutyl, n-pentyl, n-hexyl, n-heptyl, and n-octyl groups, the aryl groups represented by $R^1$ to $R^{13}$ and having 6 to 16 carbon atoms include phenyl and naphthyl, the substituted aryl groups represented by $R^1$ to $R^{13}$ include methylphenyl, ethylphenyl, propylphenyl, methoxyphenyl, ethoxyphenyl, propoxyphenyl, chlorophenyl, fluorophenyl, methylnaphthyl, methoxynaphthyl, nitronaphthyl and chloronaphthyl groups, and the aralkyl groups represented $R^1$ to $R^{13}$ and having 7 to 22 carbon atoms include benzyl, phenethyl, p-methylbenzyl, p-methoxybenzyl and p-methylphenethyl.

In the phosphine compounds of the formula (w), preferably all of $R^1$ to $R^3$ are the aryl or substituted aryl groups as defined above. However, in the phosphine compounds, one or two, preferably two, of $R^1$ to $R^3$ may be the aryl or substituted aryl groups and the remaining may be an alkyl, aralkyl or substituted aralkyl group.

The phosphine compounds of the formula (w) in which all of $R^1$ to $R^3$ are the aryl or substituted aryl groups are preferably selected from triphenylphosphine, tris (4-chlorophenyl)phosphine, tris(4-tolyl)phosphine, and α-naphtyl-(phenyl)-4-methoxyphenylphosphine.

The phosphine compounds of the formula (w) in which one or two of $R^1$ to $R^3$ are the aryl or substituted aryl groups and the remaining(s) is an alkyl, aralkyl or substituted aralkyl group, are selected from, for example, methyldiphenylphosphine, phenyl(p-methoxyphenyl) methylphosphine ethyl(phenyl)-n-propylphosphine and dimethylphenylphosphine.

In the phosphine oxide compounds of the formula (x), all of $R^4$ to $R^6$ are preferably the aryl or substituted aryl groups. However, one or two of $R^4$ to $R^6$ may be the aryl or substituted aryl groups and the other two or one may the alkyl, aralkyl or substituted aralkyl group.

The phosphine oxide compounds of the formula (x) in which all of $R^4$ to $R^6$ are the aryl or substituted aryl groups, are preferably selected from triphenylphosphine oxide, tris (4-chlorophenyl) phosphine oxide, tris (4-tolyl) phosphine oxide and a-naphthyl(phenyl)-4-methyoxyphenylphosphine oxide.

The phosphine oxide compounds of the formula (x), having one or two aryl or substituted aryl groups and two or one alkyl, aralkyl or substituted aralkyl group are preferably selected from methyldiphenylphosphine oxide, methyl(4-methoxyphenyl)phenylphosphine oxide, phenyl(p-methoxyphenyl)-methylphospline oxide, ethyl(phenyl)-n-propylphosphine oxide, ethyl(phenyl)-n-propylphosphine oxide and dimethylphenylphosphine oxide.

Among the phosphine dihalide compounds of the formula (y), it is preferable that all of $R^7$ to $R^9$ are the aryl or substituted aryl groups. However, one or two of $R^7$ and $R^9$ may be the aryl or substituted aryl groups and the other two or one of $R^7$ to $R^9$ may be the alkyl, aralkyl or substituted aralkyl group.

Also, in the formula (y), $Y^1$ and $Y^2$ may be the same as or different from each other and represent respectively a chlorine, bromine or iodine atom.

The phosphine dihalide compounds of the formula (y) in which all of $R^7$ to $R^9$ are the aryl or substituted aryl groups as defined above are preferably selected from triphenylphosphine dichloride, triphenylphosphine dibromide, triphenylphosphine diiodide.

In the phosphonium compounds of the formula (z), it is preferable that all of $R^{10}$ to $R^{13}$ are the aryl or substituted aryl groups, and $X^-$ is selected from halogen ions, aliphatic carboxylate ions and fluoroborate ion. However, in the formula (z), one to three, especially two or three of $R^{10}$ to $R^{13}$ may be the aryl and substituted aryl groups and the other one to three, especially one or two, of $R^{10}$ to $R^{13}$ may be the alkyl, aralkyl or substituted aralkyl groups, and X may be selected from halogen ions, aliphatic carboxylate ions and a fluoroborate ion.

The phosphonium compounds of the formula (z) wherein all of $R^{10}$ to $R^{13}$ are the aryl or substituted aryl groups mentioned above, and $X^\ominus$ is selected from halogen ions are preferably selected from tetraphenylphosphonium chloride, tetraphenylphosphoniuml bromide, tetraphenylphosphonium iodide, 4-chlorophenyltriphenylphosphonium chloride, 4-chlorophenyltriphenylphosphonium bromide, 4-chlorophenyltriphenylphosphonium iodide, 4-ethoxyphenyltriphenylphosphonium chloride, 4-ethoxyphenyltriphenylphosphonium bromide, 4-ethoxyphenyltriphenylphosphonium iodide, 4-methylphenyltriphenylphosphonium chloride, 4-methylphenyltriphenylphosphonium bromide, 4-methylphenyltriphenylphosphonium iodide, 9-fluorenylphenyltriphenylphosphonium chloride, and 9-fluorenylphenyltriphenylphosphonium bromide.

The phosphonium compounds of the formula (z) wherein all of $R^{10}$ to $R^{13}$ are the aryl or substituted aryl groups mentioned above, and $X^\ominus$ is selected from aliphatic carboxylate ions are preferably selected from tetraphenylphosphonium acetate, 4-chlorophenyltriphenylphosphonium acetate, 4-ethoxyphenyltriphenylphosphonium acetate and 4-methylphenyltriphenylphosphonium acetate.

The phosphonium compounds of the formula (z) wherein all of $R^{10}$ to $R^{13}$ are the aryl or substituted aryl groups mentioned above, and $X^\ominus$ is a fluoroborate are preferably selected from tetraphenylphosphonium fluoroborate, 4-chlorophenyltriphenylphosphonium fluoroborate, 4-ethoxyphenyltriphenylphosphonium fluoroborate and 4-methylphenyltriphenylphosphonium fluoroborate.

In the step (C) of the process of the present invention, the decarbonylation catalyst may consist of one or more of the above-mentioned organic phosphorus compounds. Also, the decarbonylation catalyst may be dissolved or suspended in the reaction mixture fed into the step (C).

In the step (C), the decarbonylation catalyst is preferably employed in an amount of 0.001 to 50 molar %, more preferably 0.01 to 20 molar %, based on the molar amount of the diaryl oxalate supplied to the step (C).

The decarbonylation catalyst for the step (C) containing at least one organic phosphorus-containing compound may be used together with a promoter comprising at least one member selected from inorganic halogen compounds and organic halogen compounds. Usually, the promoter halogen compound is used preferably in an amount, of 0.01 to 150 times, more preferably 0.1 to 100 times, the total molar amount of the organic phosphorus compound in the catalyst.

The inorganic halogen compounds usable as a promoter are preferably selected from halogenated aluminum compounds, for example, aluminum chloride and aluminum bromide; halogenated platinum group metal compounds, for example, platinum chloride, ruthenium chloride, and palladium chloride; halogenated phosphorus compounds, for example, phosphorus pentachloride; halogenated sulfur compounds, for example, thionyl chloride; hydrogen halides, for example, hydrogen chloride; and halogens, for example, chlorine.

The organic halogen compounds usable as the promoter are preferably selected from halogenated alkyl compounds, for example, chloroform, carbon tetrachloride, 1,2-dichloroethane and butyl chloride; halogenated aralkyl compounds, for example, benzyl chloride; halogen-substituted aliphatic carboxylic acid, for example, chloroacetic acid, and bromoacetic acid; and acid halide compounds, for example, oxalyl chloride, propionyl chloride and benzoyl chloride.

Namely, the organic halogen compounds preferably have at least one structure selected from structures (C-Hal) in which at least one halogen atom is bounded to a saturated carbon atom, and structures (-CO-Hal) in which a halogen atom is bonded to a carbonyl carbon atom. Hal represents a halogen atom, for example, a chlorine or bromine atom.

In a preferable embodiment of the liquid phase decarbonylation reaction of step (C), a diaryl oxalate and a catalyst comprising, as a principal component, an organic phosphorus compound are supplied to a reaction apparatus, and the diaryl oxalate is decarbonylated in liquid phase at a temperature of 100° to 450° C., preferably 160° to 400° C., more preferably 180° to 350° C., while removing a resultant by-product comprising carbon monoxide, to produce a corresponding diaryl carbonate. In this case, there is no limitation to the reaction pressure for the step (C). Usually, the decarbonylation reaction can be carried out under a pressure of 10 mmHg to 10 Kg.cm². Also, in the liquid phase decarbonylation reaction of step (C), a specific reaction medium is unnecessary. However, if necessary, an aprotic solvent such as diphenylether, sulfolane, N-methylpyrrolidone or dimethylimidazolidone is used as a reaction medium.

The decarbonylation reaction of step (C) is optionally carried out in gas phase. When the decarbonylation reaction of step (C) is carried out in gas phase, the catalyst for the reaction is preferably selected from those which enable the decarbonylation reaction of the diaryl oxalate to be effected at a relatively low temperature of, for example, about 200° to 600° C., and the diaryl carbonate to be obtained at a high selectivity of, for example, at least 50 molar %, particularly 60 to 100 molar %.

The decarbonylation catalyst for the gas phase reaction preferably comprises at least one alkaline earth metal oxide.

The oxides of alkaline earth metals include oxides of magnesium, calcium, strontium and barium and thermal treatment products of hydroxides, carbonates, nitrates, and sulfates of alkaline earth metals optionally in the presence of oxygen. The alkaline earth metal oxides may be in the form or a powder, particles or a shaped article and may be carried on or not carried on a carrier, for example, an alumina, silica silica-alumina or zeolite carrier.

In a preferred embodiment of the gas phase decarbonylation reaction of step (C), a material gas comprising a diaryl oxalate, and an inert gas such as nitrogen gas is supplied into a reactor at a space velocity of 10 to 10,000 $hr^{-1}$, preferably 50 to 5,000 $hr^{-1}$, and the diaryl oxalate is decarbonylated in gas phase at a reaction temperature of 300° to 500° C. to produce a corresponding diaryl carbonate. There is no limitation to the reaction pressure as long as the decarbonylation of the diaryl oxalate can be effected in gas phase. Usually, the gas phase decarbonylation reaction is preferably carried out under the ambient atmospheric pressure or a reduced pressure.

In the gas phase reaction, the diaryl oxalate in the state of a solid or a melt or a solution in a solvent is vaporized in an evaporator or an evaporating layer and the resultant vapor is introduced together with an inert gas such as nitrogen gas, into the reactor.

There is no limitation to the reactor for step (C), as long as the reactor enables the diaryl oxalate to be decarbonylated optionally in the presence of a catalyst so as to produce a diaryl carbonate together with a carbon monoxide gas. When the decarbonylation reaction is carried out in liquid phase, the reactor is preferably selected from single and multiple vessel, completely mixing type reactors (agitating vessel type reactors) and column type reactors. Also, the decarbonylation reaction is carried out in gas phase, the reactor is preferably selected from single and multiple heat exchanging tube type reactors. The materials for forming the reactors are not limited to specific types of materials, as long as the materials have a heat resistance sufficient to the decarbonylation reaction, and may be selected from, for example, glasses, stainless steels (SUS), aluminum alloys and nickel alloys.

In the liquid phase decarbonylation reaction, since the resultant reaction product-containing liquid fraction contains non-reacted diaryl oxalate and the decarbonylation catalyst, in step (D), the liquid fraction is fed in an evaporator or a thin film evaporator to separate and remove the catalyst from the diaryl carbonate, and the resultant vapor fraction containing the diaryl carbonate is fed into a conventional filler-packed column or distiller having a certain theoretical number (particularly 5 to 50) of filler-packed layers or trays, to collect the diaryl oxalate.

Alternatively, the diaryl carbonate-containing liquid fraction delivered from step (C) is distilled, in step (D), in a filler-packed column or distiller, a resultant vapor fraction comprising the diaryl carbonate is collected from the top portion of the column, and a resultant liquid fraction containing the non-reacted diaryl oxalate and the decarbonylation catalyst is withdrawn from the bottom portion from the column. The withdrawn liquid fraction is recycled into the reactor of the decarbonylation step (C).

In the step (D) as mentioned above, the diaryl carbonate is collected from the liquid fraction obtained from the liquid phase step (C). The collected diaryl carbonate has a high degree of purity.

Also, in the gas phase step (C), the resultant vapor fraction delivered from the gas phase reactor is condensed. The condensed liquid fraction contains the non-reacted diaryl oxalate and other impurities. The condensed liquid can be refined by distilling it in the above-mentioned conventional filler-packed column or distiller, and a diaryl carbonate having a high degree of purity can be easily collected.

The carbon monoxide produced in step (C) is collected and recycled into and reused in step (A) for producing the dialkyl oxalate. The collected carbon monoxide usually has a degree of purity of about 100%, and thus can be recycled into step (A) without refining. When the collected carbon monoxide contains impurities such as a hydroxyaryl compound, for example, phenol, carbon dioxide, and hydrogen chloride, due to a type of catalyst or reaction conditions, the collected carbon monoxide is refined by a simple refining apparatus, for example an absorption column or a scrubber and then fed into step (A). Also, when the reaction pressure of step (C) is lower than that of step (A), the carbon monoxide gas is pressurized by a compressor to an appropriate pressure and then supplied to step (A).

EXAMPLES

The present invention will be further explained by the following examples. In the examples, the compositions of the resultant fractions was analysed by gas-chromatography.

Example 1

Diphenyl carbonate was produced by the following procedures.

(1) Preparation of dimethyl oxalate

A stainless steel tube type reacter having an inner diameter of 27.1 mm and a height of 500 mm was packed with a solid catalyst in which 0.5% by weight of palladium is carried on α-alumina pellets having a diameter of 5 mm and a length of 3 mm. The reactor was heated so as to maintain the temperature of the catalyst layer at a level of 103° to 115° C. by flowing a heating medium through a heater surrounding the shell of the reactor. Then a material gas comprising 22.0% by volume of carbon monoxide, 10.0% by volume of methyl nitrite, 4.0% by volume of nitrogen monoxide, 5.2% by volume of methyl alcohol, 1.7% by volume of carbon dioxide, 57.1% by volume of nitrogen and pre-heated at a temperature of 90° C. by a heat exchanger was fed into a portion above the catalyst layer of the reactor by a diaphragm type gas-circulating pump at a flow rate of 1.15 $Nm^3/hr$ under a pressure of 2 $kg/cm^2G$, to produce dimethyl oxalate.

In the reactor, the material gas passed through the catalyst layer was introduced into a bottom portion of a gas-liquid contact absorption column having an inner diameter of 43 mm and a height of 1,000 mm and packed with Rasching rings. Separately methyl alcohol is introduced at a flow rate of 42 liters/hr into the contact absorption column through the top portion thereof. The material gas and methyl alcohol were brought into counter current contact with each other in the contact absorption column at a column top temperature of 30° C. and a column bottom temperature of 40° C. As a result, a condensed liquid fraction comprising 42.6% by weight of dimethyl oxalate, 1.8% by weight of dimethyl carbonate, 0.03% by weight of methyl formate, and 42.6% by weight of methyl alcohol was delivered at a flow rate of 0.3 kg/hr from the bottom portion of the column, and a non-condensed gas fraction comprising 16.2% by volume of carbon monoxide, 4.9% by volume of methyl nitrite, 8.1% by volume of nitrogen monoxide, 15.9% by volume of methyl alcohol, 1.8% by volume of carbon dioxide, and 53.1% by volume of nitrogen was delivered at a flow rate of 1.23 $Nm^3/hr$ from the top portion of the column.

The non-condensed gas fraction was mixed with 13.8 Nl/hr of oxygen and 0.5 Nl/hr of nitrogen monoxide.

The resultant mixed gas was introduced into a bottom portion of a gas-liquid contact type regeneration column having an inner diameter of 83 mm and a height of 1,000 mm and brought into counter current contact with methyl alcohol introduced through the top portion of the regeneration column at a flow rate of 0.33 liter/hr at a column top temperature of 30° C. at a column bottom temperature of 40° C., to regenerate methyl nitrite from nitrogen monoxide contained in the mixed gas. A resultant regeneration gas delivered from the top portion of the regeneration column at a flow rate of 11 $Nm^3/hr$ and comprising 18.2% by volume of carbon monoxide, 10.4% by volume of methyl nitrite, 4.2% by volume of nitrogen monoxide, 5.4% by volume of methyl alcohol, 2.0% by volume of carbon dioxide and 53.0% by volume of nitrogen, was introduced into the above-mentioned circulation pump to pressurize, to a pressure of 2.1 kg/cm²G, and then mixed with 49 Nl/hr of carbon monoxide under a pressure of 2.1 kg/cm²G. The mixed gas was fed into the above-mentioned reactor.

From the bottom portion of the regeneration column, methyl alcohol containing 5.7% by weight of water was delivered at a flow rate of 0.48 liter/hr, distilled to remove water, and then re-used as a source of methyl alcohol for the regeneration of methyl nitrite in the regeneration column.

On other hand, the condensed liquid fraction delivered from the contact absorption column was batch distilled in the amount obtained in 50 hours by a distiller having an inner diameter of 150 mm, a height of 7,500 mm, and a bottom portion capacity of 100 liter at a bottom temperature of 140° C. under a pressure of 350 mmHg. A refined dimethyl oxalate with a degree of purity of 99.9% by weight was obtained in an amount of 5.8 kg.

(2) Preparation of diphenyl oxalate

Diphenyl oxalate was produced from dimethyl oxalate produced by the above-mentioned procedure (1), as follows.

A solution comprising 54.1% by weight of phenol, 45.3% by weight of dimethyl oxalate and 0.5% by weight of tetraphenoxytitanium was fed into the twelfth step from the top of a first fifty-plate Oldershaw-type reactive distillation column provided with a one liter bottom flask and having an inner diameter of 32 mm, at a flow rate of 600 ml/hr, and the bottom flask was heated by a mantle heater to a temperature of 190° C., while withdrawing a resultant vapor fraction from the top portion of the first column at a reflux ratio of 2 and condensing the withdrawn vapor fraction by a cooler, to transesterify dimethyl oxalate with phenol and to produce diphenyl oxalate.

When the reaction in the first column was stabilized, namely 4 hours after the start of the feeding of the solution, the liquid fraction in the bottom flask comprised 6.23% by weight of diphenyl oxalate, 29.95% by weight of methyl phenyl oxalate, 23.88% by weight of dimethyl oxalate and 39.41% by weight of phenol, and was withdrawn from the bottom flask at a flow rate of 603 g/hr. Also, a resultant vapor fraction containing 99.7% by weight of methyl alcohol and 0.3% by weight of dimethyl oxalate was withdrawn from the top portion of the first column at a flow rate of about 44 g/hr.

The liquid fraction withdrawn from the bottom flask of the first column in which the transesterification of dimethyl oxalate with phenol was carried out, was fed into the twelfth step from the top of a second Oldershow type reaction distillation column in the same type as the first column, under a reduced pressure of 200 mmHg at a flow rate of 600 ml/hr, while heating the bottom flask at a temperature of 200° C. by a mantle heater and while withdrawing a resultant vapor fraction from the top portion of the second column and condensing the withdrawn vapor faction by a cooler, without refluxing, to effect a disproportionation reaction of methylphenyl oxalate into dimethyl oxalate and diphenyl oxalate.

When the reaction in the second column was stabilized, namely 4 hours after the state of the feeding, a resultant liquid fraction in the bottom flask comprised 65.27% by weight of diphenyl oxalate, 18.43% by weight of methylphenyl oxalate, 1.02% by weight of dimethyl oxalate, and 13.93% by weight of phenol, and was withdrawn from the bottom flask at a flow rate of about 258 g/hr. Also, a resultant vapor fraction containing 1.57% by weight of methyl alcohol, 2.97% by weight of dimethyl oxalate, 48.51% by weight of phenol, 2.97% by weight of methylphenyl oxalate and 0.42% by weight of diphenyl oxalate was withdrawn at a flow rate of about 371 g/hr from the top portion of the second column and condensed by a cooler.

The liquid fraction delivered from the disproportionation procedure in the second column was fed into a rotating thin film evaporator having a heat transfer area of 0.1 m² under a reduced pressure of 15 mmHg at a flow rate of 200 ml/hr, while heating the evaporator to a temperature of 200° C. by a heating mediums to continuously evaporate dimethyl oxalate, phenol, methylphenyl oxalate and diphenyl oxalate. The resultant vapor fraction was fed into a glass distiller having an inner diameter of 30 mm and a length of 2 m and packed with Helipack pellets with a diameter of 5 mm and a length of 5 mm through an inlet located 80 cm below a top of the distiller, and continuously distilled therein. A resultant vapor fraction containing 3.05% by weight of dimethyl oxalate, 41.73% by weight of phenol, and 55.21% by weight of methylphenyl oxalate was withdrawn from the top portion of the distiller at a flow rate of about 68 ml/hr, and a diphenyl oxalate vapor having a degree of purity of 99.9% by weight was withdrawn at a flow rate of about 120 g/hr from the distiller through an outlet located 40 cm above the bottom of the distiller. The collected diphenyl oxalate contained, as impurities, 0.04% by weight of phenol and 0.05% by weight of methylphenyl oxalate. Also, a liquid fraction containing the titanium compound in an amount of 2.5% by weight in terms of titanium metal was withdrawn at a flow rate of about 14 g/hr from the bottom portion of the distiller.

(3) Production of diphenyl carbonate

Diphenyl carbonate was produced from the diphenyl oxalate prepared in the above-mentioned procedures (2), as follows.

The collected diphenyl oxalate in the above-mentioned procedures (2) was mixed with 1 molar % of tetraphenylphosphonium chloride and dissolved by heating the mixture at a temperature of 150° C. The solution was fed into a reaction apparatus consisting of two glass reactors connected in series with each other and each having a capacity of one liter and equipped with a thermometer, a stirrer and an overflow pipe, at a flow rate of 300 ml/hr through a pump, while heating the two reactors at a temperature of 230° C. by a mantle heater, to decarbonylate diphenyl oxalate. The overflow pipe in each reactor was located at a level corresponding to 600 ml liquid volume contained in the reactor.

At a stage of 20 hours after the start of feeding, a liquid fraction overflowing from the second reactor (namely, passed through the decarbonylation reaction) and comprising 14.6% by weight of diphenyl carbonate, 84.0% by weight of diphenyl oxalate and 0.08% by weight of phenol was delivered at a flow rate of about 270 ml/hr from the reaction apparatus. Also, from each of the reactors, a gas fraction comprising about 100% of carbon monoxide was delivered at a total flow rate of 25 Nl/hr.

The liquid fraction delivered from the decarbonylation reaction apparatus was fed into the same type of rotating thin film type evaporator as that used in the diphenyl oxalate-preparation procedure (2), under a reduced pressure of 20 mmHg at a flow rate of 250 ml/hr, while heating the evaporator with a heating medium at a temperature of 200° C., to separate tetraphenylphosphonium chloride. The resultant distillate liquid fraction comprising 92.2% by weight of diphenyl carbonate, and 7.7% by weight of diphenyl oxalate was continuously fed into the same type of glass distiller as that used in the procedures (2) and continuously distilled under a column top pressure of 20 torr at a reflux ratio of 2.

A refined diphenyl carbonate having a degree of purity of 99.9% by weight was collected in an amount of about 220 ml/hr.

Example 2

Diphenyl carbonate was prepared by the same procedures as in Example 1, except that in the preparation (1) of dimethyl oxalate, as a portion of carbon monoxide to be supplemented to the regeneration gas for the preparation of methyl nitrite, the carbon monoxide fraction produced in the decarbonylation procedure (3) of Example 1 was employed in an amount of 25 Nl/hr. The carbon monoxide fraction was pressurized by a diaphragm type compressor to a pressure of 2.1 kg/cm$^2$G, mixed with fresh carbon monoxide gas in an amount of 24 Nl/hr under a pressure of 2.1 kg/cm$^2$G, and the mixed carbon monoxide gas was fed into the methyl nitrite-regeneration procedure.

The results of the reactions were similar to those in Example 1.

Example 3

Diphenyl carbonate was produced by the same procedures as in Example 1, except that in the dimethyl oxalate-preparation procedures (1), as a portion of methyl alcohol to be supplemented to the reaction mixture for the regeneration procedures of methyl nitrite, the withdrawn and condensed fraction from the top portion of the reactive distillation column for the transesterification procedures (2) was used. The condensed liquid fraction comprising 99.7% by weight of methyl alcohol and 0.3% by weight of dimethyl oxalate was accumulated and fed at a flow rate of 0.33 liter/hr into the top portion of the regeneration column.

The reaction results were similar to those in Example 1.

As mentioned above, in the process of the present invention, a dialkyl oxalate is prepared from carbon monoxide and at least one member selected from alkyl nitrites and alkyl alcohols, a diaryl oxalate is prepared by a reaction of the dialkyl oxalate with a hydroxyaryl compound, for example, phenol, and a diaryl carbonate is produced together with carbon monoxide by a decarbonylation reaction of the diaryl oxalate, The process of the present invention can solve the problems of the conventional non-phosgene method for producing diaryl carbonate.

In the process of the present invention, a fraction produced by the reaction of the dialkyl oxalate with the hydroxyaryl compound and comprising an alkyl alcohol can be easily collected and returned to and re-used for the production of dialkyl oxalate. Also, the carbon monoxide fraction produced by the decarbonylation reaction of the diaryl oxalate can be easily collected and returned to and reused for the production of the dialkyl oxalate. Accordingly, the process of the present invention can produce the diaryl carbonate having a high degree of purity on an industrial scale with high efficiency.

We claim:

1. A process for producing a diaryl carbonate comprising the steps of:

(A) reacting carbon monoxide with at least one member selected from the group consisting of alkyl nitrites and alkyl alcohols, to produce a dialkyl oxalate;

(B) reacting the dialkyl oxalate with a hydroxyaryl compound to produce a diaryl oxalate; and (C) decarbonylating the diaryl oxalate to produce a diaryl carbonate and a by-product comprising carbon monoxide; and (D) collecting the resultant diaryl carbonate from the reaction product mixture of step (C).

2. The process for producing a diaryl carbonate as claimed in claim 1, wherein in step (A), the reaction of the carbon monoxide with at least one member selected from the group consisting of alkyl nitrites and alkyl alcohols is carried out in the presence of a catalyst containing a platinum group metal.

3. The process for producing a diaryl carbonate as claimed in claim 1, wherein in step (A), carbon monoxide is reacted with an alkyl nitrite to produce a dialkyl oxalate and a by-product comprising nitrogen monoxide; the resultant nitrogen monoxide is recovered and subjected to a reaction with molecular oxygen and an alkyl alcohol to produce an alkyl nitrite; and the resultant alkyl nitrite is supplied to step (A).

4. The process for producing a diaryl carbonate as claimed in claim 1, wherein in step (B), (B-a) a dialkyl oxalate is subjected to a transesterification reaction with a hydroxyaryl compound in the presence of a transesterification catalyst to produce an alkylaryl oxalate and a by product comprising an alkyl alcohol, while removing the by-product comprising an alkyl alcohol to the outside of the reaction system; and (B-b) the resultant alkylaryl oxalate is subjected to at least one reaction selected from the group consisting of a disproportionation reaction and a transesterification reaction with a hydroxyaryl compound in the presence of the catalyst to produce a diaryl oxalate and a by-product comprising at least one member selected from a dialkyl oxalate and an alkyl alcohol, while removing the by-product to the outside of the reaction system.

5. The process for producing a diaryl carbonate as claimed in claim 1, wherein, in step (A), carbon monoxide is reacted with an alkyl nitrite to produce a dialkyl oxalate and a by-product comprising nitrogen monoxide, while recovering the nitrogen monoxide; in step (B), the alkyl alcohol produced as a by-product is collected and converted to an alkyl nitrite by reacting it with the nitrogen monoxide recovered in step (A) and molecular oxygen; and the alkyl nitrite is supplied to step (A).

6. The process for producing a diaryl carbonate as claimed in claim 1, wherein the carbon monoxide produced as a by-product in step (C) is recovered and supplied to step (A).

7. The process for producing a diary carbonate as claimed in claim 1, wherein the hydroxyaryl compound for step (B) is selected from the group consisting of phenol and substituted phenols having at least one substituents selected from the group consisting of alkyl groups having 1 to 6 carbon atoms, alkoxy groups having 1 to 6 carbon atoms and halogen atoms.

8. The process for producing a diaryl carbonate as claimed in claim 1, wherein the decarbonylation reaction of the diaryl oxalate in step (C) is carried out in liquid phase in the presence of a decarbonylation catalyst comprising an organic phosphorus compound.

9. The process for producing a diaryl carbonate as claimed in claim 1, wherein the decarbonylation reaction of the diaryl oxalate in step (C) is carried out in the gas phase at a temperature of 200° to 600° C.

* * * * *